| United States Patent [19] | [11] Patent Number: 4,569,793 |
|---|---|
| Dong et al. | [45] Date of Patent: Feb. 11, 1986 |

[54] CYANOHYDRINATION CATALYST

[75] Inventors: Walter Dong; Walter L. Petty, both of Houston, Tex.

[73] Assignee: Shell Oil Company, Houston, Tex.

[21] Appl. No.: 667,530

[22] Filed: Nov. 2, 1984

Related U.S. Application Data

[62] Division of Ser. No. 535,500, Sep. 26, 1984.

[51] Int. Cl.$^4$ .................. C07C 102/52; C07C 121/75; C07C 120/02; B01J 31/02
[52] U.S. Cl. .................. 260/112.5 R; 502/167; 260/465.6; 260/465 F
[58] Field of Search .................. 260/112.5 R; 502/167

[56] References Cited

FOREIGN PATENT DOCUMENTS 58-29757 2/1983 Japan .

OTHER PUBLICATIONS

Oku, J. et al., *J.C.S. Chem. Comm.*, pp. 229–230 (1981).
Oku, J. et al., *Makromol. Chem.*, 183, pp. 579–586 (1982).
Oku, J., *Kagaku Kogyo*, 32 (11), pp. 1134–1136 (62–64), Nov. 1981.

*Primary Examiner*—P. E. Konopka

[57] ABSTRACT

A cyanohydrination catalyst for the preparation of alpha-hydroxynitriles from aldehydes and ketones comprises a solid cyclo(D-phenylalanyl-D-histidine) or cyclo(L-phenylalanyl-L-histidine) dipeptide having a non-crystalline or amorphous component.

17 Claims, No Drawings

CYANOHYDRINATION CATALYST

This is a division of application Ser. No. 535,500, filed Sept. 26, 1984.

BACKGROUND OF THE INVENTION

1. Field of the Invention

The present invention relates to a cyanohydrination cyclic dipeptide catalyst, and a method of directly preparing or activating the catalysts.

2. Description of the Prior Art

Asymmetric synthesis of R-mandelonitrile by addition of hydrogen cyanide to benzaldehyde in the presence of a synthetic dipeptide catalyst is known in the art, as in Oku, Jun-ichi and Shohei Inoue, *J.C.S. Chem. Comm.*, pages 229–230 (1981), and other Oku publications where cyclo(L-phenylalanyl-L-histidine) containing ½ mole of water of crystallization was used. However, it has been found that cyclo(L-phenylalanyl-L-histidine) and cyclo(D-phenylalanyl-D-histidine) are not necessarily as satisfactory a catalyst for the preparation of certain S-α-cyano-alcohols of larger chemical structure, particularly (S)- or (R)-α-cyano-3-phenoxybenzyl alcohol and ring-substituted derivatives thereof. After encountering difficulty in obtaining high enantiomeric excesses, it was discovered that the high enantiomeric excess in the reaction to prepare (S)- or (R)-α-cyano-3-phenoxybenzyl alcohols was dependent on a particular physical form of the cyclo(L-phenylalanyl-L-histidine) and cyclo(D-phenylalanyl-D-histidine).

SUMMARY OF THE INVENTION

The present invention is directed to a catalyst for cyanohydrination of aldehydes or ketones, comprising a solid cyclo(D-phenylalanyl-D-histidine) or cyclo(L-phenylalanyl-L-histidine) having a substantially non-crystalline component. In other words, the catalyst has a component having a substantially amorphous or non-crystalline structure.

While the precise form of this cyclo(D-phenylalanyl-D-histidine) or cyclo(L-phenylalanyl-L-histidine) dipeptide is not known, it appears that in the activated (amorphous or non-crystalline) form, a number of the available —NH groups in the dipeptide are free of intermolecular hydrogen bonding to the available —C=O groups of the dipeptide crystal lattice as compared to the less active (crystalline component) form. This is believed to involve the formation of a less bonded linear or planar (or sheet) form of peptide structure as opposed to the highly bonded ribbon (or chain) form of peptide structure because of the increase in the number of —NH groups free of intermolecular hydrogen bonding to available —C=O groups in the dipeptide lattice. Such being the case, the degree of amorphousness of non-crystallinity is most readily determined by X-ray diffraction.

The wide-angle X-ray scattering (WAXS) measurements were carried out in reflection by means of a Philips APD3600/02 automated X-ray diffractometer. The samples were scanned at 20° C. in air from 5.0° to 60.0° $2\theta$ at 0.02 degree increments, and 0.6 second time increments with Cu Kα radiation (40 KV, 35ma).

The percent crystallinity was determined by a modified Hermans and Weidinger method (P. H. Hermans and A. Weidinger, *Makromol. Chem.*, 50, 98 (1961)). The diffuse background scattering below the main peaks was constructed assuming a linear baseline between $5° \leq 2\theta \leq 60°$ and approximating the amorphous scattering with a smooth curve. The X-ray crystallinity, $W_c$, was calculated from the integrated crystalline and amorphous intensities $F_c$ and $F_a$ by the equation $W_c = F_c/(F_c + F_a)$. The various definitions can be found in the text H. P. Klug and L. E. Alexander, *X-Ray Diffraction Procedures for Polycrystalline and Amorphous Materials*, Wiley-Interscience, New York, (1974).

As used herein the terms "amorphous" or "non-crystalline" define active catalyst materials which have an amorphous or non-crystalline component as determined by the area of the X-ray diffraction spectra obtained by the method described above. Preferably, the "amorphous" or "non-crystalline" component of the materials as defined by the X-ray diffraction spectra is about 45% to about 65% or higher. Preferably, the "amorphous" or "non-crystalline" component is about 65% or higher.

The catalysts are also analyzable by photomicrographs in which inefficient catalysts consist of agglomerates of fine crystallites. Crystallites are not evident in photomicrographs of active catalysts, which when, for example, are spray-dried, take the form of hollow-appearing spheres.

Alternative methods are available to define the terms amorphous and non-crystalline by infrared or nuclear magnetic resonance spectral studies or by swelling of the material, e.g. in contact with the reactants of the cyanohydrination process.

In a preferred method the dipeptide is prepared by the route described below in which HIS means histidine and PHE means phenylalanine.

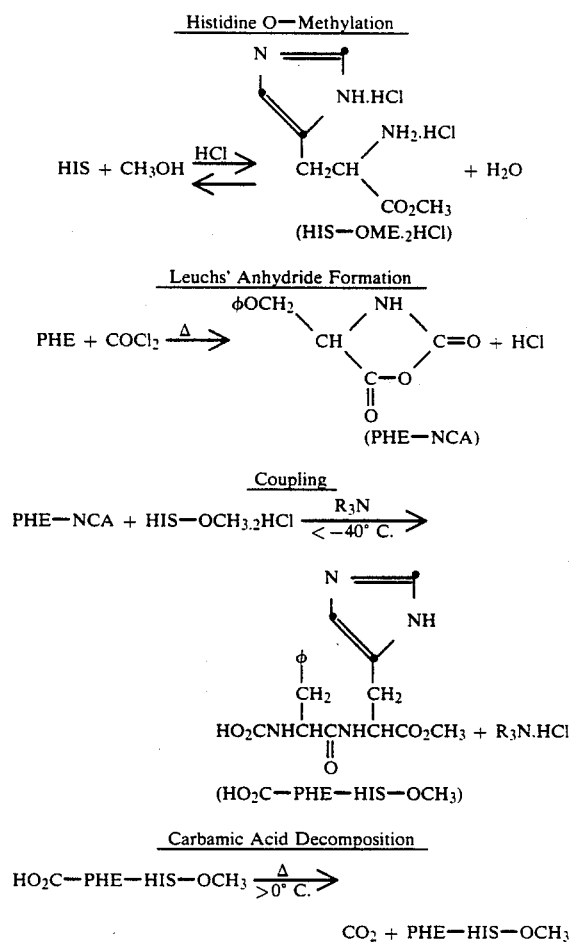

-continued

Cyclization

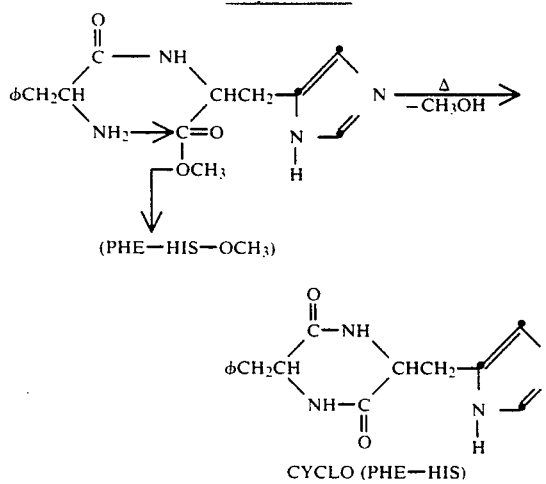

(PHE—HIS—OCH₃)

CYCLO (PHE—HIS)

The cyclo(D-phenylalanyl-D-histidine) and cyclo(L-phenylalanyl-L-histidine) dipeptide catalyst can also be prepared by other conventional peptide syntheses, for example, as in Greenstein, J. P. and M. Winitz, "Chemistry of the Amino Acids", John Wiley & Sons, Inc., New York, 1961.

When the catalyst is prepared by conventional methods in the presence of water, and as a solid, it can also contain solvent (e.g. water) of crystallization. The optically-active, cyclo(D-phenylalanyl-D-histidine) or cyclo(L-phenylalanyl-L-histidine) catalyst of the invention thus includes the presence or absence of solvent (e.g. water) of crystallization.

The solid catalyst can be recovered by extraction with acid followed by neutralization with a base or preferably by treating with (dissolving in) a solvent, for example, a hydroxylic solvent, including lower alkanols of 1 to 10 carbon atoms such as isopropanol or preferably methanol (preferably with heating, e.g. to reflux or quick flash), and reprecipitating (preferably below ambient temperature) which produces a less crystalline (or more amorphous) catalyst structure.

While it is preferred to directly prepare the catalyst of the present invention having the non-crystalline component, it is also within the scope of this invention to prepare a substantially crystalline catalyst and to subsequently activate the catalyst by converting at least part of the crystalline material to an amorphous form. Thus, the present invention is directed to both a method of directly preparing an active cyclo(D-phenylalanyl-D-histidine) or cyclo(L-phenylalanyl-L-histidine) dipeptide catalyst and to a method of activating a crystalline catalyst of this type, which methods both involve reducing or preventing the formation of a substantially crystalline form thereof. In the case of activation of a crystalline catalyst, the crystalline form is first broken down and then prevented at least in part from reforming.

It is believed that the breakdown of or the prevention of the formation of a number of intermolecular bonds between the amino N-H and the carboxyl C=O groups in the crystal lattice makes the catalyst have an amorphous or non-crystalline form. In any event, an ordered deposition of crystals of the catalyst is discouraged or reduced.

Any means which will accomplish this reduction or prevention either during the catalyst preparation or an after treatment are within the scope of the invention. Among the illustrative examples of methods which reduce or prevent the formation of a highly crystalline form or highly ordered arrangement are (a) very rapid evaporation of a solution of the catalyst, in the presence or absence of impurities or crystallinity inhibitors; (b) rapid precipitation of the catalyst from solution by dilution in a poor solvent; (c) freeze drying of a solution of the catalyst; (d) rapid cooling of the melted catalyst in the presence or absence of impurities or crystallinity inhibitors; (e) use of crystallinity inhibitors during solidification; and the like.

The unactivated dipeptide catalyst, when recovered at the end of a conventional synthesis process, is often almost completely inactive in the cyanohydrination reaction, apparently because it has become highly crystalline as can be determined by X-ray diffraction. Activation, as used herein, appears to involve converting at least part of the normally crystalline material into an amorphous form such that the dipeptide is swelled by the reaction mixture and the chiral base function of the catalyst is made accessible to the reactants. In order to produce high chirality in the cyanohydrination product, it appears that the catalyst should preferably be essentially insoluble in the cyanohydrination solvent.

The first step in converting what is or what normally would be a crystalline material to an amorphous form is to break down (or prevent) formation of the intermolecular bonds in the crystal lattice. The breakdown readily occurs when the material is melted or dissolved in a solvent. Once this has been accomplished, a method is used that will allow the separation of the dissolved material from the solvent at a rate such that normal crystallization cannot occur. There are a number of ways in which this might be effected: (a) rapid evaporation of the solvent, e.g. as in a spray dryer; (b) rapid precipitation of the material by pouring a solution of it into a large volume of a different solvent that is miscible with the original solvent but does not dissolve, to a large extent, the material to be precipitated; (c) rapid freezing of a solution followed by sublimation of the solvent (freeze drying); (d) rapid cooling of the melted catalyst; and (e) use of inhibitors alone or with any of the above methods (a)–(d). Preferably, the method used is (a) rapid evaporation of the solvent and, especially, by means of spray drying.

Because of the polar nature and high melting point (~250° C.) of cyclo(D-phenylalanyl-D-histidine) or cyclo(L-phenylalanyl-L-histidine), the choice of solvents that will dissolve it to any appreciable extent is very limited. Potential solvents suitable and unsuitable that have been tested are listed in Table 1 in order of decreasing effectiveness, and the use of these will be discussed below in relation to the method of catalyst activation via recovery techniques or specific subsequent activation treatment.

TABLE 1

| SOLVENTS TESTED FOR SOLUBILITY OF CYCLO(D-PHENYLALANYL-D-HISTIDINE) | | |
|---|---|---|
| Solvent | B.P./°C. | Solvency |
| Dimethyl Sulfoxide | 189 | Good (5–10% w) |
| Acetic Acid | 118 | Good |
| Formamide | 210 | >2.3% at 25° C. |
| 1-Methyl-2-pyrrolidinone | 202 | >2.2% at 25° C. |
| Dimethylformamide | 153 | Fair to Good, <5% at 90° C. |

TABLE 1-continued

| SOLVENTS TESTED FOR SOLUBILITY OF CYCLO(D-PHENYLALANYL-D-HISTIDINE) | | |
|---|---|---|
| Solvent | B.P./°C. | Solvency |
| Liquid Ammonia | −33 | ~2% at −40° C. |
| N—methylformamide | 185 | >2.4% at 25° C. |
| Acetonitrile | 80 | Fair to Poor, <<5% at 70° C. |
| Methanol | 64 | 1% w Hot, 0.3% w at 25° C. |
| Water | 100 | Fair to Poor, 0.1% at 25° C. |
| Acetone | 55 | Fair to Poor, <<1% at 25° C. |
| Liquid Carbon Dioxide | 78 | Poor, <0.2% at 25° C. |
| Carbon Disulfide | 45 | Very Poor |
| Diethyl Ether | 35 | Very Poor |
| Hydrocarbons | Var | Very Poor |

The use of crystallization inhibitors is an alternative method of reducing or preventing the crystalline form of the dipeptide. Many chemicals can be used. It is useful if the crystallization inhibitor has a similar kind of structure or has one or more substituents similar in kind to those found in the dipeptide, but the inhibitor is not identical to the units of the dipeptide. In the case of this dipeptide, useful kinds of crystallization inhibitors include those materials containing a —N—H and/or —C=O group, including ureas, aldehydes and amines. Even by-product impurities of the dipeptide process containing such substituents are useful crystallization inhibitors, e.g. making an impure product can make a more active catalyst.

The present invention is usefully applied to the improvement of cyanohydrination to obtain high enantiomeric selectivity, that is to a process for the preparation of optically-active alpha-hydroxynitriles or a mixture enriched therein which comprises treating the corresponding aldehyde or ketone with a source of hydrogen cyanide in a substantially water-immiscible, aprotic solvent and in the presence of a solid, cyclo(D-phenylalanyl-D-histidine) or cyclo(L-phenylalanyl-L-Histidine) dipeptide having a substantially amorphous or non-crystalline form, as a catalyst. A use of cyclo(D-phenylalanyl-D-histidine dipeptide catalysts is described in co-pending U.S. Patent Application Ser. No. 443,763, filed Nov. 22, 1982, incorporated herein by reference. An example of a use of a cyclo(L-phenylalanyl-L-histidine) dipeptide is described in Oku, Jun-ichi et al., J.C.S. Chem. Comm., pages 229-230 (1981).

A substantially water-immiscible, aprotic solvent for use in the improved cyanohydrination process of this invention is defined as an aprotic solvent in which the solubility in water is not more than 5%v at the reaction temperature (and does not interfere with the reaction). For example, the solvent is a hydrocarbon or ether solvent including acyclic, alicyclic or aromatic materials within the above definition. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable. for example, gasoline with a boiling range at atmospheric pressure of between 40° C. and 65° C., between 60° C. and 80° C. or between 80° C. and 110° C. Petroluem ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Useful ethers include diethyl ether, diisopropyl ether, methyl tert-butyl ether and the like. Preferably, the solvent is one having a boiling point of less than about 150° C. Preferably, the solvent is toluene, diethyl ether or diisopropyl ether or mixtures of toluene and one of the ethers, e.g. 25/75% of diethyl ether/toluene. Toluene gives especially high enantiomeric excess when the substrate is 3-phenoxybenzaldehyde.

The alpha-hydroxynitrile products include optically-active alpha-hydroxynitriles of formula I

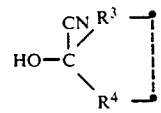

wherein $R^3$ is an optionally-substituted hydrocarbyl or heterocyclic group; and $R^4$ is an optionally-substituted hydrocarbyl group or a hydrogen atom or $R^3$ and $R^4$ together with the carbon atoms to which they are attached form a carbocyclic group as denoted by the dotted line.

Preferably, the optically-active alpha-hydroxynitrile products have the (S)-configuration, absolute or relative, when derived from aldehydes and, therefore, include (S)-alpha-hydroxynitriles of the formula II

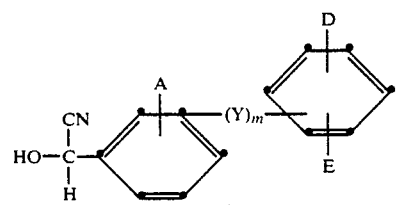

wherein m is 0 or 1; Y is O, $CH_2$, C(O), A, D and E each independently is a hydrogen atom, a halogen atom having an atomic number of from 9 to 35, inclusive, or an alkyl or alkoxy group containing 1 to 6 carbon atoms, each optionally substituted by one or more halogen atoms having an atomic number of from 9 to 35, inclusive. Preferably, Y is O and m is 1. Preferably, A, D or E each independently is a hydrogen atom, a fluorine atom, a chlorine atom, a methyl group, a trifluoromethyl group or a methoxy group. Preferably, one of D and E each is a hydrogen atom. An especially preferred embodiment of the (S)-alpha-hydroxynitriles are those of the formula above in which D is a hydrogen atom and A and E each independently is a fluorine atom or a hydrogen atom, and, preferably, when either A or E is fluorine, each is located at the 4-position of the ring relative to the benzyl carbon when A or relative to the Y=O bearing carbon atom when E. Especially suitable alcohols are when A is a fluorine atom at the 4-position and E is a hydrogen atom.

Non-limiting examples of alpha-hydroxynitriles of the above formula I include
(S)-alpha-cyano-3-phenoxybenzyl alcohol
(S)-alpha-cyano-4-fluoro-3-phenoxybenzyl alcohol
(S)-alpha-cyano-3-(4-fluorophenoxy)benzyl alcohol
and the like.

Any non-symmetrical aldehyde or ketone (carbonyl compound) is useful (provided it does not contain substituent groups which form other stable reaction products with cyanide ions or with the catalyst). Preferably, the aldehyde or ketone has the formula III

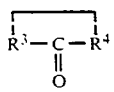

III wherein $R^3$ is an optionally substituted hydrocarbyl or heterocyclic group and $R^4$ is an optionally substituted hydrocarbyl group or a hydrogen atom, or, alternatively, $R^3$ and $R^4$ together with the carbon atom to which they are attached form a carbocyclic group and a non-symmetrical aldehyde or ketone.

The hydrocarbyl groups represented by $R^3$ and $R^4$ in the formula III may be, for example, an alkyl, a cycloalkyl or an aryl group of up to 20 carbon atoms, preferably up to 10 carbon atoms, or $R^3$ in the formula III may be a carbocyclic group. Examples of carbocyclic aryl groups are phenyl, 1-naphthyl, 2-naphthyl and 2-anthryl groups. Such aldehydes and ketone compounds are described in U.S. Pat. No. 4,132,728. Optional substituents include one or more of halogen atoms having an atomic number of from 9 to 35, inclusive, or an alkyl, alkenyl or akoxy group containing 1 to 6 carbon atoms, each optionally substituted by one or more halogen atoms; or optionally substituted phenoxy, phenyl, benzyl or benzoyl and equivalent kinds of substituents.

Preferably, an aromatic aldehyde is used of the formula IV

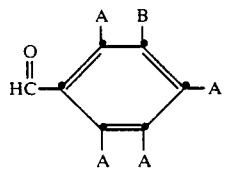

IV wherein each A is independently a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; B is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; or is group

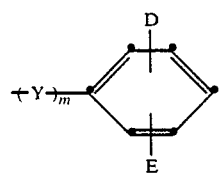

in which Y is O; $CH_2$, C(O); m is 0 or 1 and D and E each independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive.

Preferably, an aldehyde is used corresponding to the alpha-hydroxynitrile previously defined and, thus, has the formula V

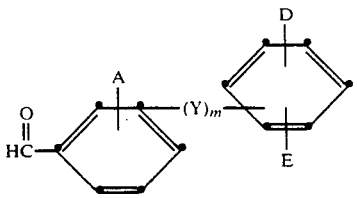

V wherein m, A, D, E and Y have the same meanings as given in the formula above.

The source of cyanide ions is hydrogen cyanide or an agent which generates hydrogen cyanide such as an alpha-hydroxynitrile such as acetone cyanohydrin, under the reaction condition. Hydrogen cyanide itself is preferred. The molar ratio of hydrogen cyanide to aldehyde or ketone is from about 1.0 to about 3.0 moles per mole of aldehyde or ketone and, preferably, from about 1.1 to about 2.0.

The amount of catalyst can vary. For example, it can be used in the range of from about 0.1 to about 5 mole percent based upon the weight of the aldehyde or ketone present, preferably about 1.0 to about 2.5 mole percent. The catalyst is preferably well dispersed in the reaction mixture.

The cyanohydrination reaction is preferably conducted by adding the aldehyde or ketone and/or solvent to the catalyst, dispersing (mechanical grinding or agitating the mixture, e.g. by stirring), adding hydrogen cyanide with or after the solvent or carbonyl compound and maintaining the reaction conditions for an amount of time to effect the formation of the optically-active alpha-hydroxynitrile. A suitable product is also made when hydrogen cyanide is added first to the catalyst, provided that the solvent and aldehyde or ketone are added immediately thereafter. The forming and maintaining of a well dispersed but not necessarily homogeneous-like reaction mixture are useful. Separation and recovery of the optically-active ester product are achieved by conventional techniques, including extraction and the like.

The temperature of the cyanohydrination reaction as well as the pressure can vary. At normal pressures, the temperature is from about −30° C. to about 80° C., more or less. Preferably, ambient temperatures of about 5° C. to about 35° C. are convenient to give good yield, rate of reaction and enantiomeric excess of the desired optically-active product, with a lower temperature of about 5° C. giving a very good selectivity.

The alpha-hydroxynitriles and their corresponding aldehydes and ketones are generally known in the literature. The (S)-cyanobenzyl alcohols are of interest per se or as intermediates to esters, e.g. of the pyrethroid type. For example, (S)-alpha-cyano-3-phenoxybenzyl alcohol in U.S. Pat. No. 4,273,727 or those described in commonly assigned U.S. Patent Application Ser. No. 443,513, filed Nov. 22, 1982. The (R)-cyanobenzyl alcohols are also pyrethroid intermediates and the resulting esters can be epimerized to the racemic or (S)-cyano alcohol esters by procedures of U.S. Pat. Nos. 4,133,826 and 4,151,195.

ILLUSTRATIVE EMBODIMENTS

The following embodiments are provided for the purpose of illustrating the invention and should not be regarded as limiting it in any way.

EMBODIMENT 1

A Niro Atomizer laboratory spray dryer with a ca 31 inch diameter chamber was assembled. In operation, 40 SCFM N$_2$ is heated to 140° C. and fed to the dryer chamber. A warm solution of 0.5–1.0%w cyclo(D-phenylalanyl-D-histidine) in methanol is fed via a rotary vaned atomizer to the chamber above the N$_2$ inlet. The droplets of cyclo(D-phenylalanyl-D-histidine) solution are rapidly dried to give hollow spherical particles of 1 to 10 μm diameter. The combined stream is fed to a cyclone where 50–70% of the particles are captured.

Six test runs were made using 5 to 10 gm of cyclo(D-phenylalanyl-D-histidine) each. Starting with a catalyst that was inefficient for cyanohydrination, all the products were activated to give good reaction rate and produce (S)-alpha-cyano-3-phenoxybenzyl alcohol with EE's between 75–80% at 97% conversion of 3-phenoxybenzaldehyde. Water and sodium chloride, simulating recycle operation, apparently had no effect on activation. On the other hand, the addition of urea to further disrupt crystallization of cyclo(D-phenylalanyl-D-histidine) did not result in any further improvement. The results of the six test runs are tabulated in Table 2.

Following procedures similar to those described in Embodiment 1 above, cyclo(L-phenylalanyl-L-histidine) is activated by spray drying.

TABLE 2

ACTIVATION OF CYCLO(D-PHENYLALANYL-D-HISTIDINE) FOR SPRAY DRYING

| Experiment | Catalyst Purity % w | Feed Composition (Rest MeOH) | | | | Feed Rate ml/min | N$_2$ Rate SCFM[f] | Temp In °C. | Temp Out °C. |
|---|---|---|---|---|---|---|---|---|---|
| | | DDCAT[d] % w | H$_2$O % w | NaCl % w | Others % w | | | | |
| 1 | 87 | 0.49 | | | | 115 | 42 | 135 | 60–75 |
| 2 | 87 | 0.48 | | | | 225 | 42 | ~160 | 60–70 |
| 3 | 92[b] | 0.84 | | | | 125 | 43 | 135–140 | 55–65 |
| 4 | 92[b] | 0.63 | 4.5 | | | 110 | 43 | 139 | 65–75 |
| 5 | 92[b] | 0.62 | 4.5 | 1.0 | | 135 | 43 | 137–140 | 55–65 |
| 6 | 92[b] | 0.65 | — | — | 0.033 | 125 | 43 | 139 | 70–75 |
| 7 | 92[b] | 0.80 | — | — | — | 135 | 42 | 135–140 | 55–70 |

| Experiment | Atomizer RPM × 10$^{-3}$ | Catalyst Recovery % | Particle Size μm | Cyanohydrination In Toluene at 25° C. | | |
|---|---|---|---|---|---|---|
| | | | | Time hr | POAL[e] Conversion % | (S)—POAL:CN[e] Selectivity[c] % |
| 1 | 37 | 46 | 1–12 | 1 | 92.2 | 91 |
| | | | | 2 | 95.9 | 90 |
| | | | | 4 | 96.9 | 90 |
| | | | | 5.5 | 95.9 | 90 |
| 2 | 31 | 58 | 1–12 | 1 | 91.3 | 90 |
| | | | | 3 | 95.5 | 88 |
| | | | | 4 | 96.7 | 88 |
| | | | | 5.1 | 98.4 | |
| 3 | 37 | 66[a] | 1–12 | 1 | 93 | 90 |
| | | | | 2 | 96.7 | 90 |
| | | | | 3 | 96.6 | 92 |
| | | | | 4 | 97.6 | 90 |
| 4 | 36 | 56[a] | 1–10 | 1 | 94.6 | |
| | | | | 2 | 96.9 | 90 |
| | | | | 3 | 98.7 | 89 |
| 5 | 36 | 68 | 1–10 | 1 | 93.6 | 91 |
| | | | | 2 | 96.6 | 90 |
| | | | | 3 | 95.4 | 91 |
| | | | | 4 | 97.5 | 90 |
| | | | | 5 | | 90 |
| 6 | 36 | 58 | 1–10 | 1 | 92.3 | 90 |
| | | | | 2 | 91.0 | 90 |
| | | | | 4 | 94.7 | 89 |
| | | | | 5 | 96.0 | 90 |
| 7 | 38 | 77 | 1–10 | 1 | 93.3 | 93 |
| | | | | 2 | 96.1 | 91 |
| | | | | 3 | 95.9 | 92 |
| | | | | 4 | 97.6 | 92 |
| | | | | 5 | 96.0 | 91 |

[a]Mostly held in cyclone by static electricity.
[b]96% purity by pot. titration.
[c]EE = 2 (selectivity) - 100. %.
[d]DDCAT = cyclo(D-phenylalanyl-D-histidine)
[e]POAL = 3-phenoxybenzaldehyde. (S)—POAL·CN = (S)—α-cyano-3-phenoxybenzyl alcohol.
[f]SCFM = standard cubic feet per minute.

EMBODIMENT 2

Table 3 summarizes the results of tests and scale-up experiments to activate the cyclo(D-phenylalanyl-D-histidine) catalyst by solvent evaporation, most of which were from methanol. Whereas the catalyst recovered by conventional crystallization was not very active, rapid evaporation of methanolic solutions was rather effective in producing active catalysts (Experiments 1–11). The addition of small amounts of impurities (5–10% basis catalyst) appeared to help prevent normal crystallization (compare Experiment 1, having no impurity, to those following it in the table). Except for dimethyl sulfoxide, all of the additives gave better results than the base case. These experiments involved rapid stripping of 25 ml of methanol from 0.2 g of catalyst in a rotating evaporator. Attempts to scale up Experiment 9 were only partially successful. The product from the first experiment had an activity/enantiomeric excess of 88%/75%, as compared to 98%/88% in the smaller experiment. The second of the large experiments was even less active, 75%/47%. Longer times required to strip off large volumes of solvent resulted in greater amounts of crystallization of the dipeptide, thus resulting in a less active material. A solution to this problem is to spray dry the solution so that the solids are recovered rapidly. Solvents that may be useful in this approach are methanol, liquid ammonia, and acetic acid.

TABLE 3

ACTIVATION OF CYCLO(D-PHENYLALANYL-D-HISTIDINE) BY SOLVENT EVAPORATION

| Experi-ment | Method of Evaporation | Temp °C. | Cyanohydrination[a] Conversion %/3 Hr | Enantiomeric Excess, % |
|---|---|---|---|---|
| 1 | Rapid small[b] evap. from methanol | ~0 | 83 | 79 |
| 2 | Rapid small evap. from methanol +5% urea | ~0 | 96 | 87 |
| 3 | Rapid small evap. from methanol, +10% 3-phenoxybenzaldeyhyde | 0-20 | 95 | 85 |
| 4 | Rapid small evap. from methanol +10% M acetic acid | 0-20 | 99 | 85 |
| 5 | Rapid small evap. from methanol, +10% $CH_3CN$ | 0-20 | 99 | 86 |
| 6 | Rapid small evap. from methanol, +10% α-isopropyl-p-chlorophenylacetonitrile | 0-20 | 97 | 87 |
| 7 | Rapid small evap. from methanol, +7% HIS—OME/triethylamine | 0-20 | 95 | 75 |
| 8 | Rapid small evap. from methanol, +50% water | 0-20 | 92 | 80 |
| 9 | Rapid small evap. from methanol, +5% filtrate residue | 0-20 | 98 | 88 |
| 10 | Rapid small evap. from methanol, +10% dimethyl sulfoxide | 0-20 | 16 | 31 |
| 11 | Rapid small evap. from methanol, +5% Z—D-PHE—HIS—OME | 0-20 | 96 | 87 |
| 12 | Slow Evaporation from hot methanol/water | 70-90 | 67 | 63 |
| 13 | Large run similar to 9 (15 g) | | 88 | 75 |
| 14 | Large run similar to 9 (15 g) | | 75 | 47 |
| 15 | Medium run similar to 9 (7 g in 2 Hr) | | 98 | 86 |

[a]Cyanohydrination of 3-phenoxybenzaldehyde with HCN to give (S)—alpha-cyano-3-phenoxybenzyl alcohol.
[b]Small means 0.2 g of catalyst in 25 ml of solvent.

EMBODIMENT 3

Solvent precipitation is another way of activating the cyclo(D-phenylalanyl-D-histidine) dipeptide, and Table 4 summarizes some results using this approach. In all but one example shown, dimethyl sulfoxide (DMSO) was used to dissolve the catalyst as a 5% solution, and the dipeptide was precipitated by pouring this solution into a well-stirred vessel of second solvent, under a variety of conditions. In most cases, the precipitated catalyst formed a voluminous gel which was rinsed with the second solvent to remove dimethyl sulfoxide and blown dry. In Experiments 5-14 urea (5% basis catalyst) was added to the DMSO solution to aid in preventing crystallization of the dipeptide. In any case, from the results shown, it appears that (a) of the five precipitating solvents tested, dichloromethane and toluene appeared to be best; (b) high temperature (80° C.) gave better results than lower temperature (25° C.); (c) high dilution gave a better result than lower dilution (compare Experiments 5 and 6); and (d) the catalyst precipitated from liquid ammonia solution (Experiment 4) was moderately active (82% conversion in 3 hours) and quite selective (84% EE, even after 22 hours of contact with the catalyst). Unlike all of the others this product was a dense solid that was easy to filter and wash. A number of solvents for cyclo(PHE-HIS) shown in Table 1 can be used in this approach, namely, DMSO, acetic acid, formamide, 1-methyl-2-pyrrolidinone, dimethylformamide, N-methylformamide, liquid ammonia, and the like.

TABLE 4

ACTIVATION OF CYCLO(D-PHENYLALANYL-D-HISTIDINE) BY SOLVENT PRECIPITATION

| Experi-ment | Method of Precipitation | Cyanohydrination[d] Conversion %/3 Hr | Enantiomeric Excess, % |
|---|---|---|---|
| 1 | From dimethyl sulfoxide (5%) into diethyl ether | 65 | 41 |
| 2 | From dimethyl sulfoxide (5%) into toluene, 80° C. | 97 | 72 |
| 3 | From dimethyl sulfoxide (5%) into toluene 25° C., large scale | 74 | 37 |
| 4 | From liquid $NH_3$ (2%) into diethyl ether, −40° C. | 82 | 84[b] |
| 5 | From dimethyl sulfoxide[a] into 20 V toluene, 25° C. | 42 | 31 |
| 6 | From dimethyl sulfoxide into 5 V toluene, 25° C. | 4 | 10 |
| 7 | From dimethyl sulfoxide into 20 V toluene, 80° C. | 85 | 57 |
| 8 | From dimethyl sulfoxide into 20 V acetonitrile, 80° C./25° C. | 77 | 37[c] |
| 9 | From dimethyl sulfoxide into 20 V acetonitrile, 25° C. | 2 | 18[f] |
| 10 | From dimethyl sulfoxide into 20 V tetrahydrofuran, 25° C. | 2 | 19[g] |
| 11 | From dimethyl sulfoxide into 20 V diethyl ether, 25° C. | 2 | 0[c] |
| 12 | From dimethyl sulfoxide into 20 V dichloromethane | 77 | 49 |
| 13 | From dimethyl sulfoxide into 20 V tetrahydrofuran + 1% v/v $H_2O$, 25° C. | 77 | 60 |
| 14 | Experiment 13 and vacuum oven dried | 89 | 50[h] |

[a]Catalyst 5% w/v in dimethyl sulfoxide, urea 5% basis catalyst.
[b]After 22 hours at 95% conversion.
[c]After 71 hours the enantiomeric excess was 24% at a conversion of 97%.
[d]Cyanohydrination of 3-phenoxybenzaldehyde with HCN to give (S)—alpha-cyano-3-phenoxybenzyl alcohol.
[e]At 92% conversion.
[f]At 44% conversion.
[g]At 49% conversion.
[h]After 4 hours.

EMBODIMENT 4

Another method tested for activating the catalyst is freeze drying. This approach requires a solvent for the dipeptide that freezes at a convenient temperature and is volatile enough to be sublimed at below that temperature and at a practical pressure (vacuum). Of the solvents tested, only water and acetic acid meet these requirements. The results of some of these tests are summarized in Table 5. Freeze drying of a 0.1%w solution of the dipeptide in water gave an excellent product (Experiment 5). An attempt to freeze dry a solution in dimethyl sulfoxide failed because the solvent was too high boiling to be sublimed at about 0° C. and 170 microns pressure. On the other hand, solutions in glacial acetic acid were readily freeze dried. The product from this freeze drying contains one mole of acetic acid per mole of catalyst. In spite of this, the product was surprisingly active and selective (Experiment 2). This acid is relatively loosely held by the catalyst, and it was volatilized away in a sweep of air, on the one hand (Experiment 3), or neutralized by triethylamine treatment, on the other (Experiment 4). In both cases the products had about the same activity/selectivity: 93%/72%.

TABLE 5

ACTIVATION OF CYCLO(D-PHENYLALANYL-D-HISTIDINE) BY FREEZE DRYING

| Experiment | Solvent/Work Up | Cyanohydrination[c] | |
|---|---|---|---|
| | | Conversion %/3 Hr | Enantiomeric Excess, %[b] |
| 1 | From 2% solution in dimethyl sulfoxide | — | |
| 2 | From 1.9% solution in acetic acid | 74 | 56 (6.5) |
| 3 | Product from experiment 2 air swept 2 days | 93 | 73 (5) |
| 4 | Product from Experiment 2 treated with triethylamine in diethyl ether | 93 | 72 (6.3) |
| 5 | From 0.1% solution in water | 98 | 85 (2.5) |

[a]Solution frozen at −40° C.; solvent sublimed at 0.1 Torr.
[b]Numbers in parentheses indicate time, in hours.
[c]Cyanohydrination of 3-phenoxybenzaldehyde with HCN to give (S)—alpha-cyano-3-phenoxybenzyl alcohol.

Following procedures similar to those described in Embodiment 4 above, cyclo(L-phenylalanyl-L-histidine) is activated by freeze drying.

What is claimed is:

1. A process of directly preparing a solid cyclo(D-phenylalanyl-D-histidine) or cyclo(L-phenylalanyl-L-histidine) dipeptide catalyst to obtain an active catalyst for use in chiral cyanohydrination which comprises forming a substantially non-crystalline or amorphous component of at least 45% or more of the dipeptide by a method selected from (a) rapidly evaporating a solution of the catalyst; (b) rapidly precipitating the catalyst from a solution by dilution in a poor solvent; (c) freeze drying of a solution of the catalyst; (d) rapid cooling of a melted catalyst; or (e) using crystallinity inhibitors during solidification.

2. A process according to claim 1 wherein 65% or higher of the dipeptide is an amorphous or non-crystalline component.

3. A method according to claim 2 wherein the activation method is (a) rapid evaporation of a solution of the catalyst.

4. A method according to claim 3 wherein the rapid evaporation is by spray drying.

5. A process according to claim 1 wherein the method is (a) rapidly evaporating a solution of the catalyst.

6. A process according to claim 1 wherein the method is (b) rapidly precipitating the catalyst from a solution by dilution in a poor solvent.

7. A process according to claim 1 wherein the method is (c) freeze drying of the solution of the catalyst.

8. A process according to claim 1 wherein the method is (d) rapid cooling of a melted catalyst.

9. A process according to claim 1 wherein the method is (e) using crystallinity inhibitors during solidification.

10. A process for producing a cyanohydrination catalyst of high enantiomeric selectivity which comprises forming a solid cyclo(D-phenylalanyl-D-histidine) or cyclo(L-phenylalanyl-L-histidine) dipeptide catalyst having a substantially non-crystalline or amorphous component of at least 45% or more of the dipeptide by a method selected from (a) rapidly evaporating a solution of the catalyst; (b) rapidly precipitating the catalyst from a solution by dilution in a poor solvent; (c) freeze drying of the solution of the catalyst; (d) rapid cooling of a melted catalyst; or (e) using crystallinity inhibitors during solidification.

11. A process according to claim 10 wherein 65% or higher of the dipeptide is an amorphous or non-crystalline component.

12. A process according to claim 11 wherein the method is (a) rapid evaporation of a solution of the catalyst.

13. A process according to claim 12 wherein the rapid evaporation is by spray drying.

14. A process for increasing the enantiomeric selectivity of a cyanohydrination catalyst which comprises forming a solid cyclo(D-phenylalanyl-D-histidine) or cyclo(L-phenylalanyl-L-histidine) dipeptide catalyst having a substantially non-crystalline or amorphous component of at least 4590 or more of the dipeptide by a method selected from (a) rapidly evaporating a solution of the catalyst; (b) rapidly precipitating the catalyst from a solution by dilution in a poor solvent; (c) freeze drying of a solution of the catalyst; (d) rapid cooling of a melted catalyst; or (e) using crystallinity inhibitors during solidification.

15. A process according to claim 14 wherein 65% or higher of the dipeptide is an amorphous or non-crystalline component.

16. A method according to claim 15 wherein the method is (a) rapid evaporation of a solution of the catalyst.

17. A method according to claim 16 wherein the rapid evaporation is by spray drying.

* * * * *

UNITED STATES PATENT AND TRADEMARK OFFICE
CERTIFICATE OF CORRECTION

PATENT NO. : 4,569,793
DATED : February 11, 1986
INVENTOR(S) : WALTER DONG and WALTER L. PETTY It is certified that error appears in the above-identified patent and that said Letters Patent are hereby corrected as shown below:

Cover Sheet (page 1), in Section [62], change "1984" to -- 1983 --.

Claim 14, line 6, change "4590" to -- 45% --.

Signed and Sealed this

Thirteenth Day of May 1986

[SEAL]

Attest:

Attesting Officer

DONALD J. QUIGG

Commissioner of Patents and Trademarks